United States Patent [19]

Andrews

[11] 4,097,993
[45] Jul. 4, 1978

[54] ORTHODONTIC ARCH WIRE

[75] Inventor: Lawrence F. Andrews, San Diego, Calif.

[73] Assignee: "A"-Company, Inc., San Diego, Calif.

[21] Appl. No.: 784,227

[22] Filed: Apr. 4, 1977

[51] Int. Cl.² .............................................. A61C 7/00
[52] U.S. Cl. .................................................... 32/14 A
[58] Field of Search ................... 32/14 B, 14 A, 14 R, 32/17; 29/160.6

[56] References Cited

U.S. PATENT DOCUMENTS

| 2,566,414 | 9/1951 | Henry | 32/14 A |
| 3,261,181 | 7/1966 | Scott | 29/160.6 |
| 3,526,961 | 9/1970 | Kesling | 32/14 A |

OTHER PUBLICATIONS

"Dental Arch Form Related with Intraoral Forces: PR=C", American Journal of Orthodonics, vol. 61, No. 6, pp. 558–559, 6-1972.

*Primary Examiner*—Robert Peshock
*Assistant Examiner*—John J. Wilson
*Attorney, Agent, or Firm*—Townsend and Townsend

[57] ABSTRACT

An orthodontic arch wire having a generally U-shaped configuration including a pair of legs that are generally symmetrical about a mid-point of the arch wire. Each of the legs is composed of a plurality of circular segments of varying radius wherein the point of transition between contiguous segments lies on a common line tangential to both segments.

8 Claims, 4 Drawing Figures

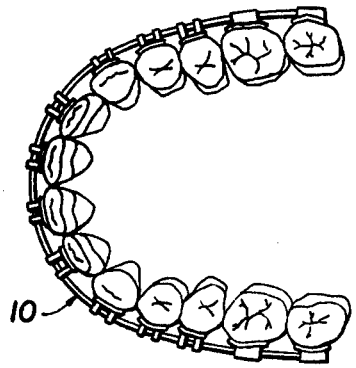
FIG._1.
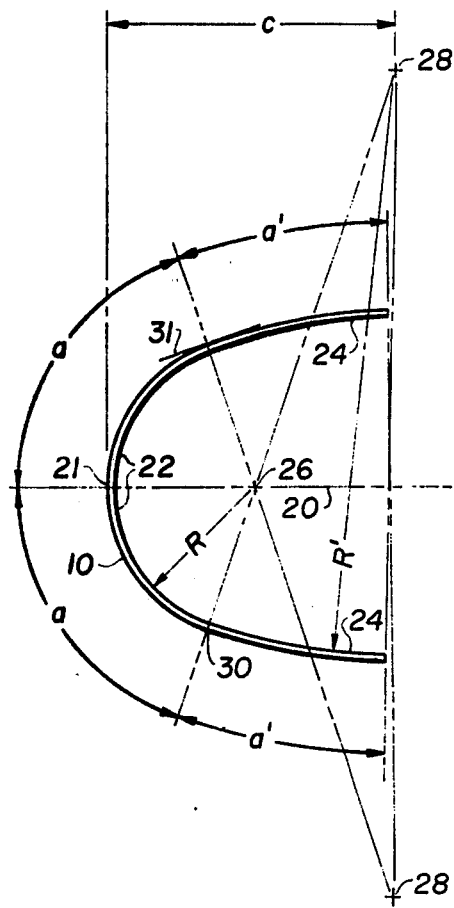
FIG._2.
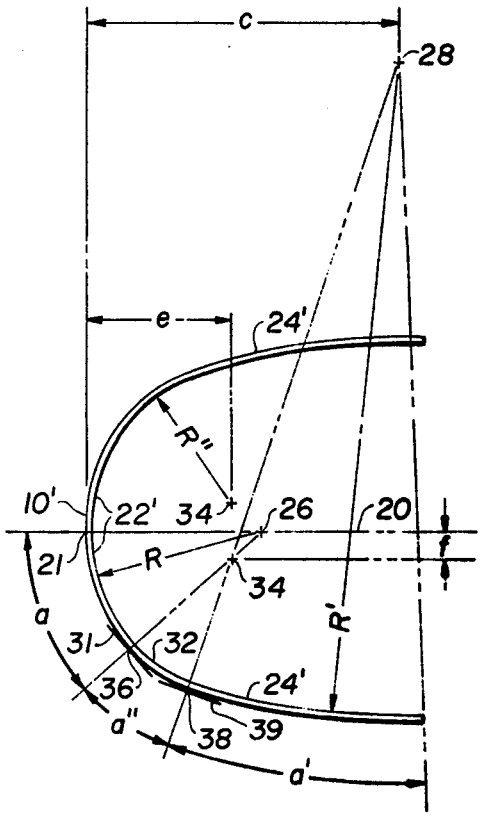
FIG._3.
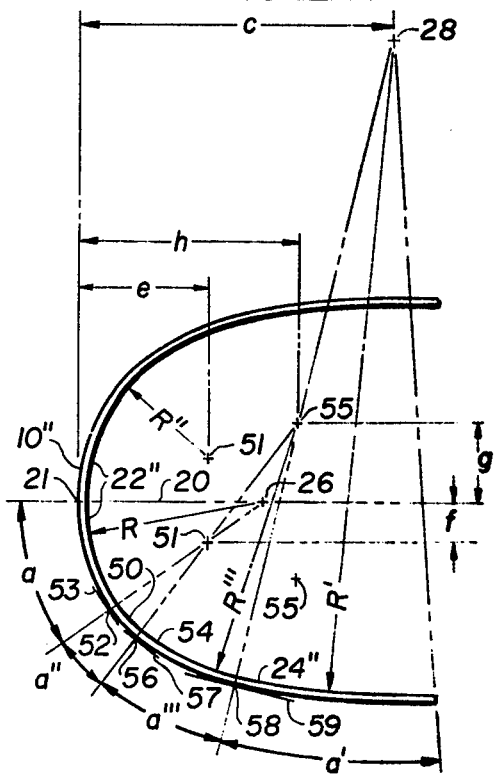
FIG._4.

ORTHODONTIC ARCH WIRE

BACKGROUND OF THE INVENTION

The present invention relates to an orthodontic arch wire for use with orthodontic brackets mounted at about the middle of the clinical crown of each of a plurality of teeth. More particularly, the arch wire form of this invention is especially useful with tooth-mounted orthodontic brackets of the type described in U.S. Pat. No. 3,660,900, issued May 9, 1972, wherein the location of the groove is generally defined by a horizontal plane intersecting approximately the mid-point of the long axis of the clinical crown of the tooth.

Among the objectives of those specializing in orthodontia is to produce normal occlusion of teeth through relocation thereof by forces created by various forms of mechanical appliances. Such mechanical appliances have long included brackets suitable for attachment either directly to a tooth or to a band surrounding an individual tooth or a pad that is adhesively secured to an individual tooth. The brackets are conventionally formed with a rectangular groove in the outer face thereof for receipt of an arch wire. The orthodontist inserts the arch wire in the grooves of the tooth-mounted brackets and then applies what he considers to be appropriate corrective forces to each tooth by bending the arch wire on either side of an individual bracket.

More recently, various approaches have been developed to minimize the amount of time heretofore required for handbending of the orthodontic arch wire. Such approaches have involved pre-forming the arch wire with predetermined bends designed to minimize the amount of hand-bending required to produce the corrective forces considered by the arch wire designer to be necessary to attain ideal occlusion.

Typical of such pre-formed arch wires are those provided by the process disclosed in U.S. Pat. No. 2,566,414 which issued on Sept. 4, 1951. The purpose of this patented technique was to provide the orthodontist with an arch wire having a symmetry corresponding to what the inventor had determined to be an average arch so that further hand-bending would be minimized. U.S. Pat. No. 2,566,414 disclosed apparatus and a process for forming a standardized arch wire with a number of divisions of varying curvature, offset in relation to each other so as to conform to the inventor's characterization of what should constitute the proper arch symmetry of an average size set of teeth. Additionally, provision was made for pre-torquing the arch wire (1) by forming the arch wire with dies having predetermined surface inclination and (2) by rolling the arch wire in the plane of the finished arch.

Furthermore, a dental arch form has been proposed that consists of a compound curve representing a steady state of equilibrium delimited by what was calculated to be the counterbalancing force field of the tongue and of the circumoral tissues as applied at the outermost portion of each tooth. Such a dental arch form is intended to approximate the unique geometry of a closed curve having trifocal elliptic properties, with the teeth occupying only a portion of the total curve at its constricted end; see American Journal of Orthodontics, Volume 61, No. 6, pages 541–561, June, 1972.

A further arch wire form has now been discovered that exhibits unexpectedly superior results when utilized to apply corrective forces to teeth through orthodontic brackets where the brackets are located on the teeth so that the grooves lie on a plane generally extending through about the middle of the clinical crown of each tooth. More particularly, it has now been found that, with the aforementioned bracket mounting position, there is an arch wire, pre-formed from a series of unique contiguous circular segments, that substantially eliminates the need for the orthodontist to hand-bend the dental arch wire form once an appropriate size of arch form has been selected.

Thus, it is a principal object of this invention to provide a specialized dental arch wire form that is particularly suitable for use with the type of bracket disclosed in the aforementioned U.S. Pat. No. 3,660,900, when each of such brackets is applied so that the groove therein lies at about the middle of the clinical crown of the respective tooth being treated.

BRIEF DESCRIPTION OF THE DRAWINGS

FIG. 1 is a top plan view of a typical installation of an arch wire of this invention interconnected with brackets having in/out correction and attached at about the middle of the clinical crown of the respective teeth;

FIG. 2 is a top view of a preferred form of this invention as applied to the lower jaw, illustrating the geometric relationship between the contiguous circular segments forming the arch wire;

FIG. 3 is a top view of a preferred form of arch wire for application to the upper jaw; and FIG. 4 is a top view of a further improved form of arch wire for application to the upper jaw.

DETAILED DESCRIPTION OF VARIOUS EMBODIMENTS OF THE INVENTION

Referring now to the drawings, wherein similar characters of reference represent corresponding parts in each of the several views, there is shown in FIG. 1 rectangular arch wire 10 as it is intended to be engaged with the grooves of a series of orthodontic brackets mounted at about the middle of the clinical crown of a corresponding number of teeth. The brackets have been provided with an amount of in/out correction as described in U.S. Pat. No. 3,660,900. Arch wire 10 is typically 0.018 × 0.025 inches for engagement with a bracket with a correspondingly sized groove.

FIG. 2 depicts a typical arch wire 10 of this invention, especially suitable for application to brackets attached as hereinbefore described to the teeth of the lower jaw. Arch wire 10 has a median axis 20 and a mid-point 21 about which it is symmetrical. Lower jaw arch 10 is composed of a pair of inner segments 22 extending outwardly from midpoint 21 and a pair of outer segments 24, each extending outwardly from respective of inner segments 22 from transition point 30, common both to inner segment 22 and outer segment 24, as hereinafter more particularly described.

Inner segments 22 are each defined from a single center of curvature 26 and by a single radius of curvature R. Outer segments 24 each are defined from a separate center of curvature 28 and a separate radius of curvature R'. Center of curvature 28 is located so as to lie on a straight line passing through center of curvature 26 and transition point 30. In this manner, transition point 30 also falls on a line 31 tangential to both of contiguous segments 22 and 24, i.e., line 31 is perpendicular to both radius of curvature R and R'. As a result, a smooth uninterrupted transition is accomplished from one circular segment 22 of one radius R to a second circular segment 24 of a different radius R'.

The length (in degrees of arc) of each inner segment 22 is designed to enable that portion of arch wire 10 to engage the grooves in brackets attached to the central incisor, lateral incisor and cuspid teeth on a respective side of a patient's lower jaw. It has been found that all size variations can be accommodated by a small, medium and large arch wire size, as hereinafter further described. However, typical of the length of inner segment 22 is an arc a defined by an angle in the range of 71°–72°. Similarly, outer segment 24 typically has a length defined by an arc a' having an angle in the range of 18°–22°. Generally it has been found necessary for the radius of curvature R of inner segment 22 and the radius of curvature R' of outer segment 24 to be in a length ratio of about 1:4.

FIG. 3 illustrates a typical arch wire form 10' of this invention for use on either a small or medium sized upper jaw. Arch wire 10' is also defined by a median axis 20 and mid-point 21. The small upper jaw arch wire 10' is composed of a pair of inner segments 22' extending outwardly from mid-point 21, a pair of intermediate segments 32 extending outwardly from respective of inner segments 22' at transition points 36 and a pair of outer segments 24', extending outwardly from respective of intermediate segments 32 at transition points 38.

Inner segments 22' are again each defined from a single center of curvature 26 and by a single radius of curvature R. Outer segments 24' each are again defined from a separate center of curvature 28 and a separate radius of curvature R'. Intermediate segments 32 each are defined from a separate center of curvature 34 and a separate radius of curvature R''. Center of curvature 26 is located so as to lie on a straight line passing through center of curvature 34 and transition point 36. In this manner, transition point 36 also falls on a line 31 tangential to both of contiguous segments 22' and 32. Similarly, center of curvature 28 is located so as to lie on a straight line passing through center of curvature 34 and transition point 38. In this manner, transition point 38 falls on a line 39 tangential to both of contiguous segments 32 and 24'. As a result, a smooth uninterrupted transition is accomplished from one circular segment 22' of one radius R through a second circular segment 32 of a different radius R'' to a third circular segment 24' of a different radius R'.

The length (in degrees of arc) of each inner segment 22' is designed to enable that portion of arch wire 10' to engage the grooves in brackets attached to the central incisor and lateral incisor on a respective side of a patient's upper jaw. The length (in degrees of arc) of intermediate segment 32 is designed to enable that portion of arch wire 10' to engage the groove in the bracket attached to the cuspid on a respective side of a patient's upper jaw. Typical of the length of inner segment 22' is an arc a defined by an angle in the range of 40°–52°. Typical of the length of intermediate segment 32 is an arc a'' defined by an angle in the range of 19°–31°. Similarly, outer segment 24' typically has a length defined by an arc a' having an angle in the range of 19°–22°. Generally, it has been found necessary for the radius of curvature R of inner segment 22' and the radius of curvature R' of outer segment 24' to be in a length ratio of about 1:4.

FIG. 4 illustrates a typical arch wire form 10'' of this invention for use on a large upper jaw. Arch wire 10'' is also defined by a median axis 20 and mid-point 21. The large upper jaw arch wire 10'' is composed of a pair of inner segments 22'' extending outwardly from mid-point 21, a pair of first intermediate segments 50 extending outwardly from respective of inner segments 22'' at transition points 52, a pair of second intermediate segments 54 extending outwardly from respective of first intermediate segments 50 at transition points 56, and a pair of outer segments 24'', extending outwardly from respective of second intermediate segments 54 at transition points 58.

Inner segments 22'' are again each defined from a single center of curvature 26 and by a single radius of curvature R. Outer segments 24'' each are again defined from a separate center of curvature 28 and a separate radius of curvature R'. First intermediate segments 50 each are defined from a separate center of curvature 51 and a separate radius of curvature R''. Second intermediate segments 54 each are defined from a separate center of curvature 55 and a separate radius of curvature R'''.

Center of curvature 26 is located so as to lie on a straight line passing through center of curvature 51 and transition point 52. In this manner, transition point 52 also falls on a line 52 tangential to both of contiguous segments 22'' and 50. Similarly, center of curvature 55 is located so as to lie on a straight line passing through center of curvature 51 and transition point 56. In this manner, transition point 56 falls on a line 57 tangential to both of contiguous segments 50 and 54. Still further, center of curvature 28 is located so as to lie on a straight line passing through center of curvature 55 and transition point 58. In this manner, transition point 58 is caused to fall on a line 59 tangential to both of the contiguous segments 54 and 24''. As a result, a smooth uninterrupted transition is accomplished from circular segment 22'' of one radius R through circular segment 50 of a different radius R'' through circular segment 54 of a different radius R''' to circular segment 24'' of a different radius R'.

The length (in degrees of arc) of each inner segment 22'' is designed to enable that portion of arch wire 10'' to engage the grooves in brackets attached to the central incisor and lateral incisor on a respective side of a patient's upper jaw. The length (in degrees of arc) of first intermediate segment 50 is designed to enable that portion of arch wire 10'' to engage the groove in the bracket attached to the cuspid on a respective side of a patient's upper jaw. The length (in degrees of arc) of second intermediate segment 54 is designed to enable that portion of arch wire 10'' to engage the groove in the bracket attached to the bicuspids on a respective side of a patient's upper jaw. Typical of the length of inner segment 22'' is an arc a defined by an angle in the range of 33°–34°. Typical of the length of first intermediate segment 50 in an arc a'' defined by an angle in the range of 19°–20°. Typical of the length of second intermediate segment 54 is an arc a''' defined by an angle in the range of 23°–24°. Generally, it has been found necessary for the radius of curvature R of inner segment 22'' and the radius of curvature R' of outer segment 24'' to be in a length ratio of about 1:4.

The following chart tabulates typical dimensions and angles for arch wires of this invention designed for application to small, medium and large lower and upper jaws. The dimensions are in inches and angles in degrees. The letters of reference relate to corresponding letters of reference in FIGS. 2, 3, and 4 of the drawings.

| Arch Wire Dimensions/ | Lower Jaw Arch Wire | | | Upper Jaw Arch Wire | | |
|---|---|---|---|---|---|---|
| Angles | Small | Medium | Large | Small | Medium | Large |
| Width | 2.180 | 2.256 | 2.330 | 2.360 | 2.440 | 2.520 |
| Length | 1.825 | 1.950 | 2.075 | 2.010 | 2.135 | 2.260 |
| Inner Segment Radius (R) | .920 | .958 | .995 | 1.033 | 1.080 | 1.125 |
| Inner Segment Arc ~ (a) | 71.394 | 71.741 | 71.372 | 51.394 | 40.236 | 33.367 |
| Outer Segment Radius (R') | 3.700 | 3.738 | 3.775 | 4.145 | 4.145 | 4.145 |
| Outer Segment Arc (a') | 18.498 | 19.731 | 21.164 | 19.583 | 21.108 | 17.714 |
| Axis Distance of R' from Mid-Point (c) | 1.832 | 1.854 | 1.908 | 1.990 | 2.017 | 1.970 |
| First Middle Horizontal Offset Segment (e) | — | — | — | .852 | .910 | .816 |
| First Middle Segment Arc (a') | — | — | — | 19.299 | 30.287 | 19.320 |
| First Middle Segment Radius (R") | — | — | — | .703 | .825 | .725 |
| First Middle Segment Vertical Offset (f) | — | — | — | .258 | .180 | .250 |
| Second Middle Horizontal Offset Segment (h) | — | — | — | — | — | 1.380 |
| Second Middle Segment Arc (a''') | — | — | — | — | — | 23.611 |
| Second Middle Segment Radius (R''') | — | — | — | — | — | 1.655 |
| Second Middle Segment Vertical Offset (g) | — | — | — | — | — | .490 |

Although the present invention has been described with reference to particular embodiments, it is to be understood that modifications and adaptations may be made without departing from the spirit and scope of the present invention, as set forth in the claims.

What is claimed is:

1. An arch wire adapted to engage the grooves in a set of tooth-mounted orthodontic brackets that have been applied at about the middle of the clinical crown of respective teeth, said arch wire being symmetrical about a mid-point and formed of a plurality of contiguous circular segments on each side of said mid-point, the length and curvature of each said segment being sufficient to engage the groove of at least one of said tooth-mounted orthodontic brackets, the point of transition between respective said contiguous segments being defined by a common line tangential to said contiguous segments.

2. An arch wire in accordance with claim 1 wherein said plurality of segments comprises an inner and outer contiguous segment.

3. An arch wire in accordance with claim 2 wherein the radius of curvature of said inner and outer segments is in a ratio of about 1:4.

4. An arch wire in accordance with claim 2 wherein the length of said inner segment is defined by an angle in the range of 71°–72°.

5. An arch wire in accordance with claim 1 wherein said plurality of segments comprises an inner, intermediate and outer contiguous segment.

6. An arch wire in accordance with claim 5 wherein the length of said inner segment is defined by a first angle in the range of 40°–52° and the length of said intermediate segment is defined by a second angle in the range of 19°–31° with the proviso that the sum of said first and second angles is in the range of 70°–71°.

7. An arch wire in accordance with claim 1 wherein said plurality of segments comprises an inner, first intermediate, second intermediate and outer contiguous segment.

8. An arch wire in accordance with claim 4 wherein the length of said inner segment is defined by a first angle in the range of 33°–34°; the length of said first intermediate segment is defined by a second angle in the range of 19°–20°; and the length of said second intermediate segment is defined by a third angle in the range of 23°–24°.

* * * * *